United States Patent
George et al.

(10) Patent No.: US 7,101,382 B2
(45) Date of Patent: Sep. 5, 2006

(54) RETRACTABLE SCALPEL

(76) Inventors: Samuel George, 4 Ronneby Close, Webridge, Surrey KT13 9SB (GB); Mike Hoftman, 22205 Dardenne Ave., Calabasas, CA (US) 91311

(*) Notice: Subject to any disclaimer, the term of this patent is extended or adjusted under 35 U.S.C. 154(b) by 488 days.

(21) Appl. No.: 10/706,354

(22) Filed: Nov. 12, 2003

(65) Prior Publication Data

US 2004/0098004 A1    May 20, 2004

Related U.S. Application Data

(60) Provisional application No. 60/425,866, filed on Nov. 12, 2002.

(51) Int. Cl.
*A61B 17/32* (2006.01)

(52) U.S. Cl. .......................... 606/167; 30/162

(58) Field of Classification Search .............. 606/167, 606/166, 170, 172, 174; 30/2, 158, 162, 30/62, 164, 151, 339
See application file for complete search history.

(56) References Cited

U.S. PATENT DOCUMENTS

| | | | |
|---|---|---|---|
| 5,431,672 A * | 7/1995 | Cote et al. .................... 606/167 |
| 5,531,754 A | 7/1996 | Shackelford, Sr. et al. |
| 5,571,127 A * | 11/1996 | DeCampli .................... 606/167 |
| 5,908,432 A * | 6/1999 | Pan ............................. 606/167 |
| 6,022,364 A | 2/2000 | Flumene et al. |
| 6,949,109 B1 * | 9/2005 | Iske et al. .................... 606/167 |

* cited by examiner

*Primary Examiner*—Kevin T. Truong

(57) ABSTRACT

The present invention is a retractable scalpel device with two releasable latching elements. When the scalpel blade is in an extended position, each releasable latching element is accessible for depression by finger pressure to cause retraction of the extended blade. However, the releasable latching elements are located on opposite edges (top and bottom edges) of a cover housing and about halfway along its length. The releasable latching elements must be depressed at the same time for the extended scalpel blade to be retracted into the cover housing.

15 Claims, 5 Drawing Sheets

RETRACTABLE SCALPEL

This application is a continuation in part of Ser. No. 60/425,866 filed Nov. 12, 2002 now abandoned.

BACKGROUND OF THE INVENTION

The present invention relates to disposable scalpels and, in particular, to retractable-blade types thereof.

Medical personnel, especially highly skilled surgeons, are at risk every day from accidental stabbing. Scalpels must be passed from one person to another and back again in surgical procedures. In addition, a surgeon may retain a scalpel in his grasp while trying to use another instrument such as a hemostat or retractor or to adjust an overhead lamp, making it highly likely that an accidental incision or laceration will cause undue harm to a patient or other medical personnel whose hands are nearby.

Injuries arising from the above accidents are known as "sharps" injuries. Medical personnel are always at risk of contracting potentially fatal bacterial and/or, viral infections, including HIV and Hepatitis B and C. It is desirable to cover or shield a scalpel blade when the scalpel is not specifically being used for cutting in a desired place and process.

The simplest way to protect an exposed scalpel blade is cover it with material that won't be subject to being cut when the cover is in place. However, a wide preference among surgeons for scalpels with non-covered blades leads to a single and simple conclusion. The mechanisms and structures in the prior art used to effectively cover scalpel blades are not being used because they unduly interfere with or distract the surgeon. Such surgeons find that they would rather accept a terrible risk of infection to themselves and harm to the patient instead of accepting the reduced surgical performance available from covered blade scalpels that have covers that can be removed before and replaced after use. In many, if not most, prior art blade covers, just the act of removing or replacing the cover exposes the surgeon to risk of injury from the blade.

One type of scalpel with a blade cover are those that cause the blade to be retracted into a cover housing. The cover housing is essentially the scalpel handle. Several serious design challenges arise almost immediately when a scalpel blade must be retracted into a scalpel handle. The mechanism incorporates a spring so that, when released, the blade is automatically withdrawn into the handle. Means are required to maintain the blade in its extended position against the retractive bias of the spring.

U.S. Pat. No. 5,531,754 describes a retractable blade mounted on a blade holder mechanism housed within a cover housing. The housing has regularly-spaced notches while the blade holder mechanism includes a resilient spring clip that is biased against the sheath. When the spring clip engages with a notch, the blade is held in position until pressure is exerted on the spring clip to release the blade for extension or retraction with respect to the sheath. Once extended from the handle, the retractable blade of U.S. Pat. No. 5,431,672 is locked in place by pivoting a button. The button includes a shaped post that, when in one position, allows movement of the blade into and out of the handle but prevents movement of the blade when the button is pivoted through 900. The blade may be permanently locked within the handle by movement of the blade holder mechanism to its fullest extent and over a cleat. The cleat prevents further movement of the blade into or out of the handle so the whole device may be disposed of safely.

U.S. Pat. No. 6,022,364 describes a retractable blade with a rocker switch. The switch includes an internal molding that latches over a bar within the handle to prevent movement of the blade into or out of the handle. Accidental emergence of the blade from the handle is limited by a depression in the internal face of the handle which receives the internal molding of the switch when the blade is fully retracted within the handle.

All the blade locking devices described in the prior art are designed for quick and simple release of a blade so it is automatically retracted within a sheath or handle where its cutting edge and sharp point are protected. However, the Applicant has discovered that these quick-release locks present a substantial problem during surgery when the stability and reliability of surgical implements is of paramount importance. In particular, the Applicant has found that the locks are too easily released, causing accidental retraction of a blade within its handle. The application of the rocker switch described in U.S. Pat. No. 6,022,364 requires a single action with no fallback lock, cover or protection. Indeed, the switch may not be locked properly over the internal bar so an accidental knock of the switch will allow the blade to retract into the handle. Similarly, the pivotable button of U.S. Pat. No. 5,431,672 may not be engaged properly and may be knocked accidentally or worked round during use of the scalpel, thereby allowing accidental retraction of the blade while in use.

It will be appreciated that such accidental retraction of a blade is not only inconvenient but may cause serious injury to the user as well as to a patient. It also breaks the user's concentration and requires the user to interrupt the surgical procedure to re-set or check the blade.

SUMMARY OF THE INVENTION

The present invention is a retractable scalpel device with two releasable latching elements that eliminate accidental blade retraction.

The invention comprises a cover housing with a long slider cavity containing a sliding piece. An actuator extends laterally from the sliding piece through a longitudinal slot in the cover housing The sliding piece can be moved forward and rearward by moving the actuator along the slot in the cover housing. The sliding piece is also spring loaded so that the sliding piece is urged rearward when a user moves the actuator in a forward direction.

A scalpel blade extends forward from its effective and supportive connection with the sliding piece. The scalpel blade can therefore be moved by the actuator in forward and rearward directions. In moving to a forwardmost position, the scalpel blade is moved point first through an end opening of the cover housing and is sufficiently exposed so that all surgical procedures typical of that type of blade may be performed thereafter. Upon reaching the forwardmost position, the releasable latching elements spring into openings in the cover housing to form an effective and secure latch for the objects of all surgical procedures. In moving rearward from a forwardmost position, the blade is retracted into the cover housing and may be entirely protected by the cover housing.

The sliding piece is connected at a rearward point to one end of a spring. The other spring end is connected with a rearward part of the interior of the cover housing. When the scalpel blade is in an extended position, each releasable latching element is accessible for depression by finger pressure to cause retraction of the extended blade. However, the releasable latching elements are located on opposite edges (top and bottom edges) of a cover housing and about halfway along its length. The releasable latching elements must be depressed at the same time for the extended scalpel blade to be retracted into the cover housing. Because the releasable latching elements are located in a low profile elevation with respect to the outside surface of the cover housing, the releasable latching elements cannot be inadvertently be depressed simultaneously to result in accidental blade retraction.

In addition, locating the releasable latching elements on top and bottom edges and about halfway down a length of the cover housing virtually eliminates accidental release. In use, the cover housing is essentially the scalpel handle and a user will firmly compress a forward part of that cover housing with their thumb and opposing fingers. A user may accidentally depress a bottom edge of the cover housing in vigorous downward strokes of the scalpel. However, simple ergonomics of the human palm eliminates the possibility of the releasable latching element on the top edge from being depressed at the same time. In such vigorous downward strokes of a scalpel, the thumb presses sideways against a left and forward side of the cover housing, the index finger presses on the opposite right side of the cover housing, the other fingers may curl around the bottom edge of the cover housing, and the lower and fleshy part of the palm below the ring and little fingers presses on a rearward top edge and right side of the cover housing.

The above extreme condition of the use of the invention scalpel is ineffective in causing accidental release of the invention scalpel blade. The user's hand in this extreme condition has their concave part of their palm directly over the releasable latching element located on the top edge of the cover housing and about halfway down its length. No matter how hard a user must compress the cover housing with their hand, the user's hand will not cause a release of the top edge releasable latching element.

Another aspect of the invention is a permanent latch for the sliding piece. The sliding piece bears the scalpel blade and the releasable latching elements. The sliding piece is further connected to a spring urging the sliding piece to be retracted into the cover housing when both releasable latching elements are released. In one form of the permanent latch, strong spring force acts on the sliding piece when it is released from a forward position with the blade exposed. The spring force in that case is sufficient to drive the sliding piece rearward into non-releasable connection with a rear part of a cavity of the cover housing. After achieving that non-releasable connection, the blade on the sliding piece is safely enclosed by the cover housing and cannot thereafter be moved forward. Alternately, a user may use an actuator extending from the sliding piece to force it into such a non-releasable connection. The permanent latch permits a final securing of the blade within the cover housing and eliminates accidental stabbing if the actuator is moved into a forward position.

BRIEF DESCRIPTION OF THE DRAWINGS

FIG. 9 is a left direction view of the left section of the cover housing with the sliding piece in a rest position.

FIG. 10 is a left direction view of the left section of the cover housing.

FIG. 11 is a right direction view of the right section of the cover housing with the sliding piece in latched, blade exposed position having no spring loading of the sliding piece.

FIG. 12 is a left direction view of the left section of the cover housing with the sliding piece in a latched, blade exposed position with the sliding piece spring-urged in a rearward direction.

FIG. 13 is the device of FIG. 12 where a permanent latch secures the sliding piece in a non-releasable position.

FIG. 14 is the device of FIG. 13 with a alternate form of the permanent latch.

FIG. 15 is section 53 of FIG. 14 showing the relationship of the actuator with the sliding piece.

DETAILED DESCRIPTION OF THE INVENTION

Figure 1:
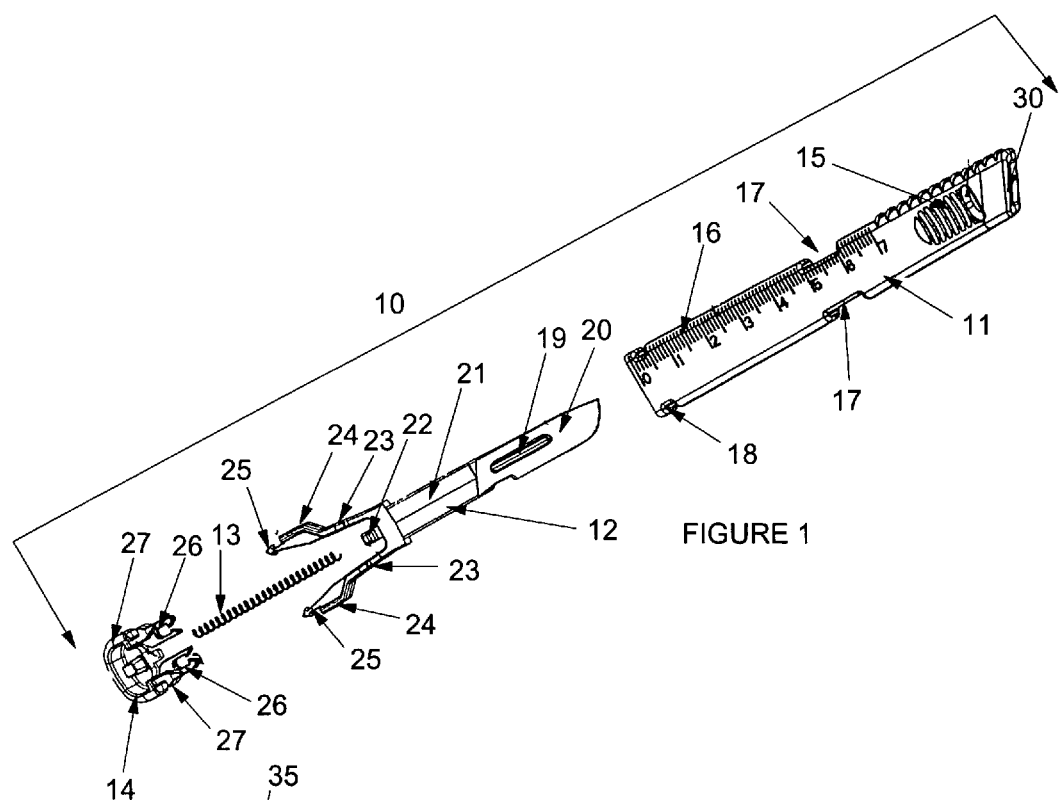
FIGS. 1 and 2 are respectively right and left side exploded views of the invention

The invention is now discussed with reference to the figures. FIGS. 1 through 8 show several aspects of the invention retractable scalpel. The scalpel 10 comprises a cover housing (with housing 11 and end cap 14), a scalpel blade 20, a sliding piece 12, and a spring 13. The assembled scalpel 10 is shown in FIGS. 3, 4, 6, 7, and 8.

Figure 2:
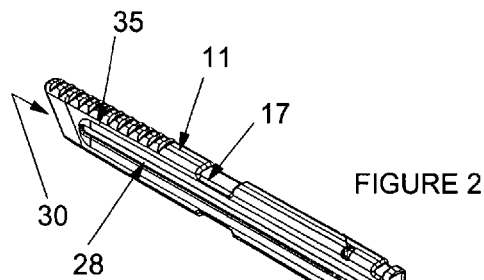
Figure 2:
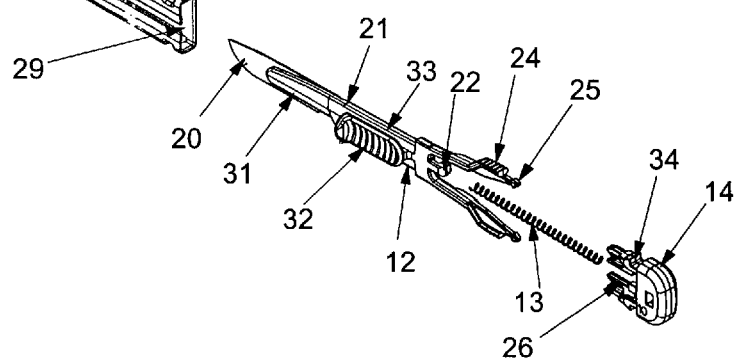
Figure 3:
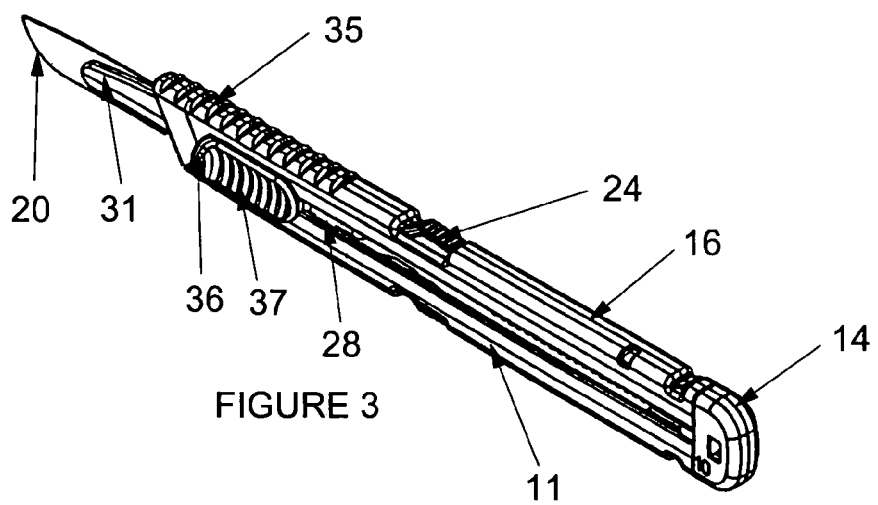
FIGS. 3 and 4 are respectively a top, rearward perspective and right side views of the assembled invention scalpel.
Figure 4:
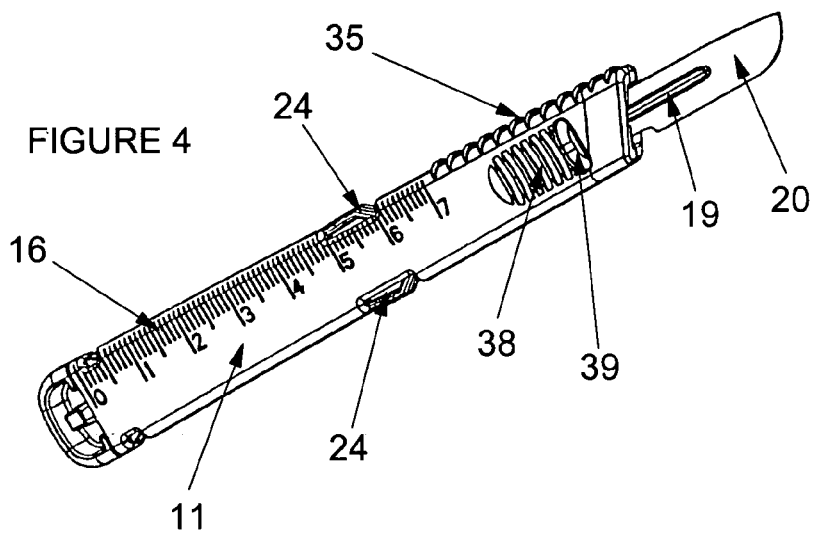
Figure 5:
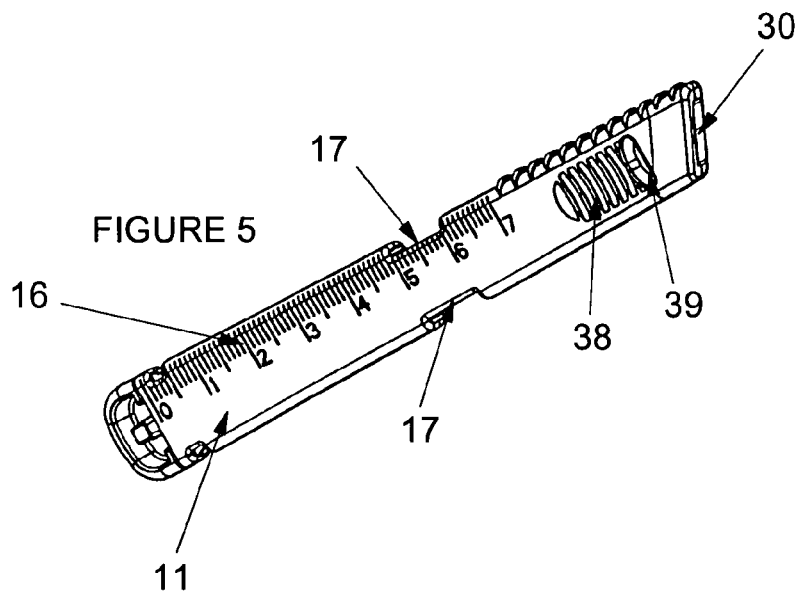
FIG. 5 is a right side view of the cover housing.
Figure 6:
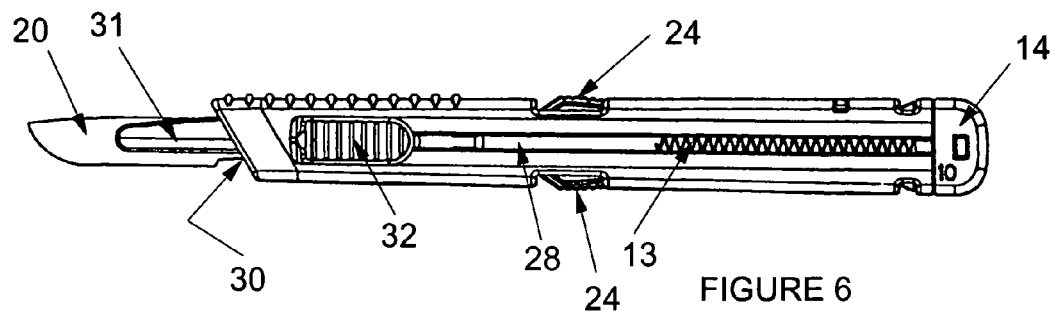
FIGS. 6, 7 and 8 are respectively left side, top, and right side views of the assembled invention scalpel.
Figure 7:
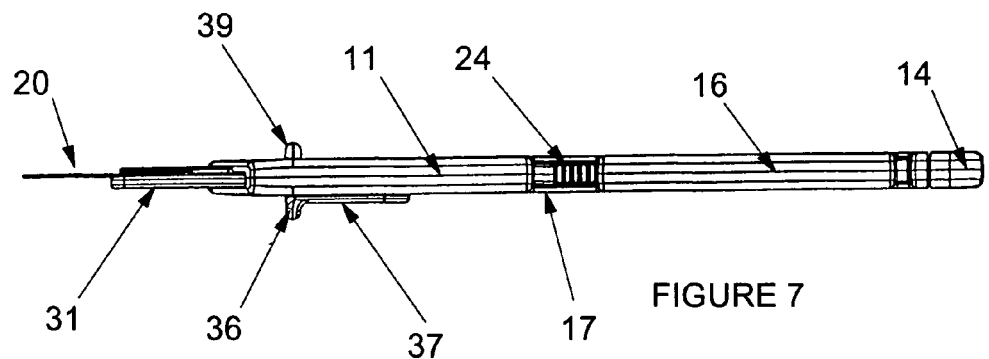
Figure 8:
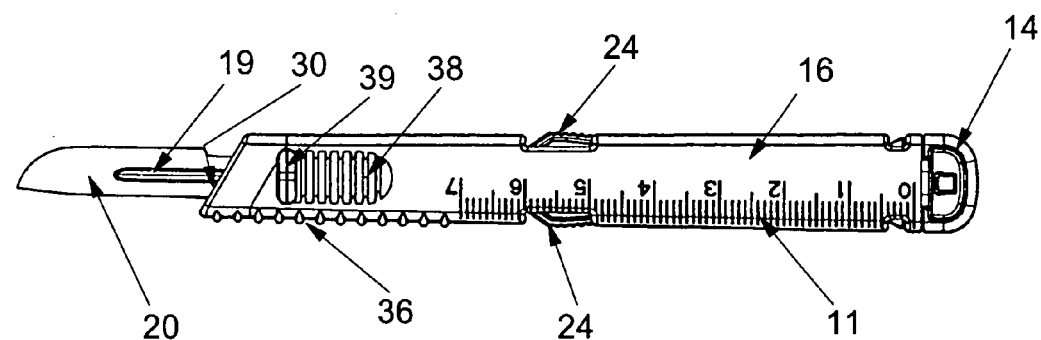
Figure 15:
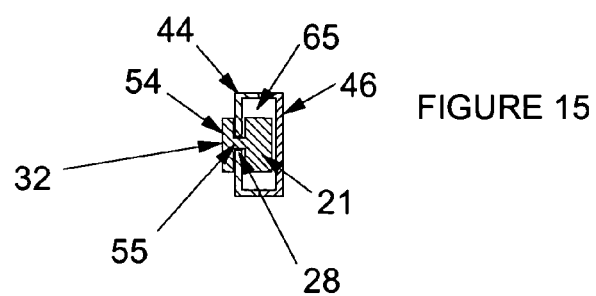

The cover housing is generally formed like a scalpel handle. It may not be thicker than about three eighths of an inch and is preferably about one fourth of a inch or less. This limitation has in the past condemned retractable scalpels to be either too thick (sufficient structural support) or too thin (the handle part is too flexible and bends too much during critical steps in a procedure). The present invention has achieved exceptional resistance to bending while maintaining a desired thickness of the cover housing. Housing 11 comprises a generally rectangular shape with a bore extending from opening 30 to opening 29, where slot 28 extends from opening 29 to just short of opening 30. FIG. 15 shows that connector 55 of actuator 32 extends inward from thumb piece 54 through slot 28 to mid section 21 of sliding piece 12. This connection of the actuator 32 with mid section 21 defines a support bracket 33 (as shown in FIG. 2). It is a critical aspect of the invention that bracket 33 be designed with sufficiently close tolerances so that blade 20 does not waver up and down or sideways in use, as shown in FIG. 3.

Housing 11 also comprises finger grip 35 on a top and forward part thereof. A second finger grip 15, with forward raised rib 39 and concave ribs 38, are adapted for engaging a forefinger or middle finger of a user. In a similar an mirror image manner, the left facing surface of thumb piece 54 is formed with a forward raised rib 36 and concave ribs 37. When actuator 32 is in a forwardmost and latched position, thumb piece 54 and finger grip 15 are aligned on opposite sides of housing 11.

Figure 9:
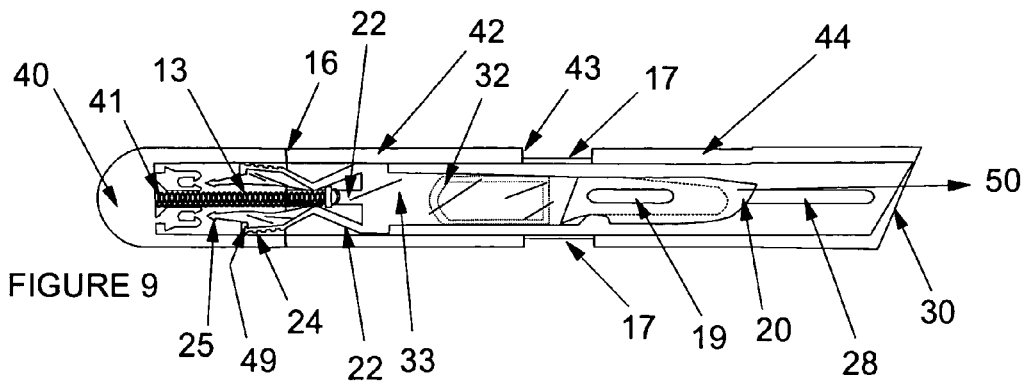
FIGS. 9 to 15 show an alternate form of the cover housing, where the cover housing is formed as right and left longitudinal sections.
Figure 10:
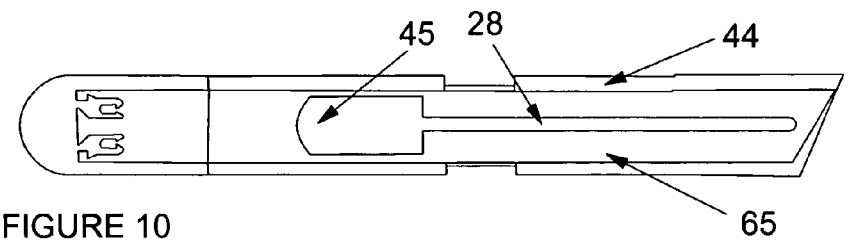
Figure 13:
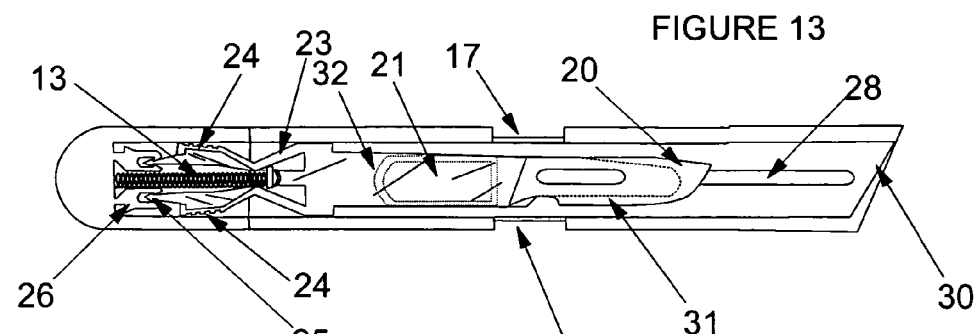

Housing 11 comprises openings 18 to receive tabs 34 (in FIG. 2) to lock end cap 14 into opening 29. Permanent latch pieces 26 extend forward on end cap 14, and are shown in FIGS. 9, 10 and 13 in unlatched and latched states with sliding piece 12. Spring 13 is adapted to be connected at one end with end cap 14 and at the other end to connector 22 of sliding piece 12. As described above, spring 13 (which may be any sufficiently elastic piece) urges sliding piece 12 rearward when actuator 32 is moved forward from a rest point. As used herein, a rest point is that state for the scalpel where the spring force of spring 13 on sliding piece 12 is essentially zero. The rest point will always be similar to that shown in FIGS. 5 and 9.

Sliding piece 12 comprises a forward part 31 with connection means 19 for engaging a slot in blade 20. This type of secure connection of a scalpel blade with a scalpel is well known. Sliding piece 12 further comprises a mid section 21. Mid section 21 is the support from which laterally extends actuator 32. Actuator 32 comprises connector 55 (as in FIG. 15) that extends from a left side of mid section 21 and through slot 28 of the cover housing.

Figure 11:
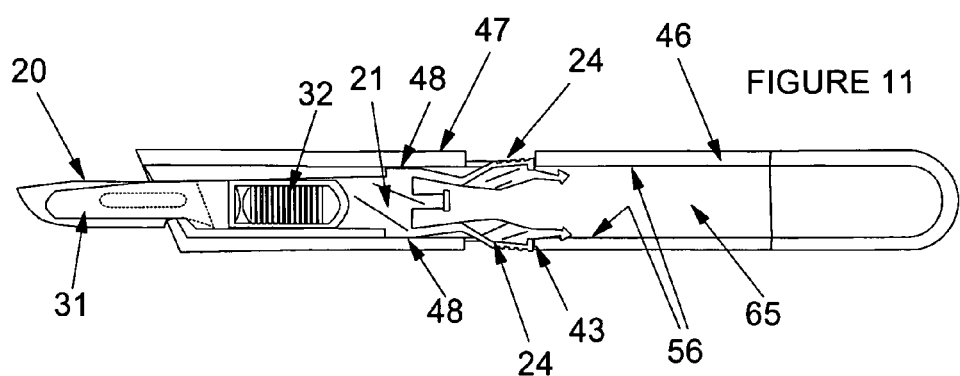
Figure 12:
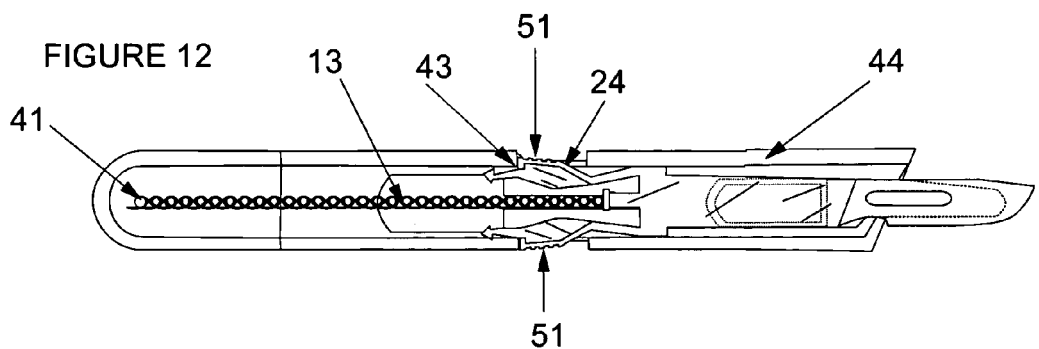

U-shaped leg section 23 contains several important aspects of sliding piece 12. The forward part of section 23 is widened compared with mid section 21 so that the top and bottom surfaces of that forward part engage the top and bottom surfaces of the sliding cavity within the cover housing. FIG. 11 shows interfaces 48 are sliding interfaces of the forward part of section 23 with the inside surfaces 56 of cavity 65. These interfaces 48 combine with bracket 33 connection with slot 28 to provide substantially all the support between the cover housing and the blade fixed to the sliding piece 12. It has been found that such sparse support is effective for all necessary surgical procedures, even ones where the activities must be vigorous, as described above.

Rearward from the forward part of section 23 are legs from which extend releasable latching elements 24 and permanent latching elements 25. The legs are formed so that elements 24 spring into openings 17 in housing 11 when actuator 32 is moved into a releasable latching position, as shown in FIGS. 3, 4, 6, 7, 8, 11 and 12. In that position, blade 20 is exposed in a manner required for surgical procedures typical of that type of blade. A rear surface 43 of opening 17 abuts a notch in elements 24 preventing rearward travel of sliding piece 12 unless both elements 24 are depressed in direction 51 (as in FIG. 12) so that elements 24 move below an innermost edge of surface 43. FIG. 9 shows that sliding piece 12 (and therefore blade 20) move in direction 50 when actuator 32 is moved in a forward direction.

Figure 14:
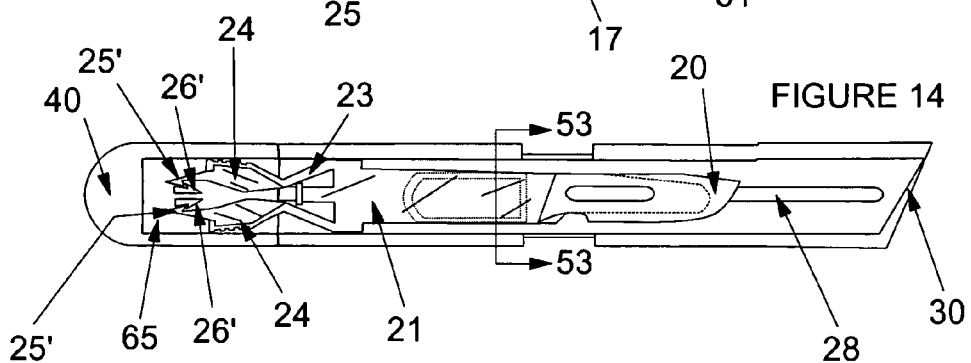

When elements 24 move below an innermost edge of surface 43, spring 13 urges sliding piece 12 rearward. FIG. 9 shows that sliding piece 12 may return to a rest point. FIGS. 13 and 14 show that sliding piece 12 may be engaged with permanent latching means so that blade 20 may not be exposed unless the cover housing is broken apart.

FIGS. 13 and 14 show that latch pieces 26 and 26' are respectively adapted to permanently capture the ends of permanent latching elements 25 and 25'. In one form of the permanent latches of the invention, when elements 24 are released from openings 17, spring 13 pulls at sliding piece 12 so hard that the ends of permanent latching elements 25 and 25' are respectively driven into permanent capture by latch pieces 26 and 26'. Alternately, a user may move the actuator 32 in a rearward position from a rest point and force the ends of permanent latching elements 25 and 25' into permanent capture by latch pieces 26 and 26'.

FIGS. 9 through 15 show an alternate embodiment of the cover housing. Right section 46 is formed by a molding operation of a single piece and comprises the internal and external features of the cover housing formed from a right side of housing 11 and end cap 14. Left section 44 is formed by a molding operation of a single piece and comprises the internal and external features of the cover housing formed from a left side of housing 11 and end cap 14, with the following exception. After molding formation, left piece 44 defines an opening 45 extending from a rearward end of slot 28. To assemble the invention scalpel 10, sliding piece 12 with attached blade 20 is aligned so that thumb piece 54 is inserted through opening 45 from a right side (the inside surface of cavity 65). When thumb piece 54 is so inserted, a left side of sliding piece 12 abuts a right side of cavity 65 of section 44 and sliding piece 12 is moved forward so that connector 55 effectively engages slot 28. Section 46 can the be permanently joined with section 44 to form the invention cover housing.

Figure 16:
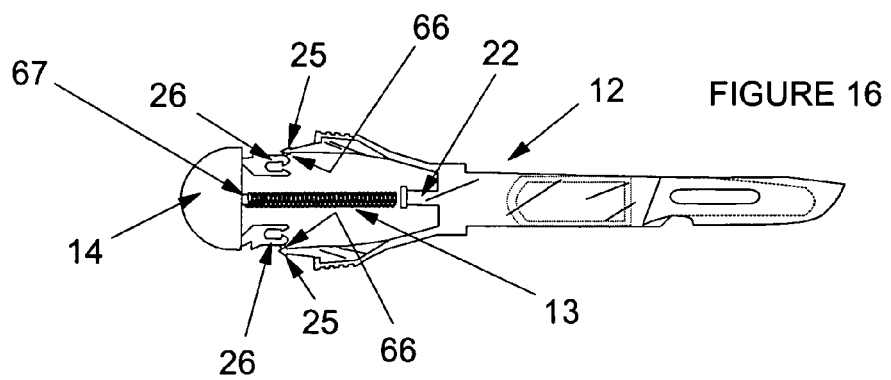
FIG. 16 shows a number of methods of molding the sliding piece, end cap and spring of FIG. 1 to reduce operation steps.

The invention includes manufacturing steps to produce one or more parts of the retractable scalpel. FIG. 16 shows the end cap 14 and sliding piece 12 are joined at breakable tabs 66. Tabs 66 join at inward sides of permanent latching elements 25 and lateral sides of latching piece 26. These connections at tabs 66 allow sliding piece 12 and end cap 14 to be formed in a single molding step, where molten resin flows between mold cavities for sliding piece 12 and end cap 14 through a passage formed for tabs 66. Forming sliding piece 12 and end cap 14 in a single molding step reduces assembly costs since the unitary piece shown in FIG. 16 of sliding piece 12, tabs 66 and end cap 14 can be broken apart at tabs 66 for further assembly of scalpel 10. FIG. 16 shows the result of placing one end of spring 13 within a part of the mold cavity for extension 22 before the molding operation. After that molding operation, the end of spring 22 within the cavity for extension 22 is permanently embedded in extension 22, reducing fabrication costs and eliminating the possibility that spring 13 might accidentally get loose from its preferred connection with extension 22. Another form of the invention steps of FIG. 16 joins extension 22 with extension 67 with an elastomer strap to replace in structure and function spring 13. After first molding sliding piece 21 and end cap 14, a second molding step connects the ends of extension 22 and extension 67 with the elastomer strap. This second step eliminates the fabrication step of manually attaching the ends of spring 13 to extensions 22 and 67.

The invention sliding piece may be formed from solid polymer, a relatively heavy material secured in a polymer casing, or a solid piece of relatively heavy material such as metal (i.e., iron or lead). Adding weight to disposable scalpels is preferable to give a surgeon a device more familiar to the surgeon. The typical re-usable scalpel typically has a familiar weight, a weight to which a surgeon has become accustomed.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

We claim:

1. A retractable scalpel device comprising:
   (a) a cover housing with top and bottom edges and right and left sides along a length of the cover housing, the cover housing formed in substantially the shape of a surgical scalpel handle and defining a longitudinal sliding bore, the sliding bore having a blade opening defined in the cover housing at a forward end, a closed end at a rear end of the cover housing, and a slot extending through at least part of the left side of the cover housing;
   (b) a sliding piece comprising a forward section, on which is fixed a scalpel blade, a mid section, and a U-shaped legs section, where the mid section has a lateral extension through the slot and beyond the left side of the cover housing to form an actuator substantially wider than the slot adapted to permit a user to move the sliding piece in forward and rearward motion in the slot and within the sliding bore;

(c) the legs section comprising a sliding section with lateral dimensions substantially wider and thicker than the mid section and adapted to slidingly support the sliding piece in the sliding bore;

(d) the legs section further comprising two flexible legs extending rearward from the sliding section, where a rearward part of the legs are urged apart from one another and have a releasable latching element urged against either a top or bottom surface of the sliding bore;

(e) spring means for urging the sliding piece rearward so that in a rearward rest position the blade is covered by the cover housing and in a forward latched position the blade has passed though the blade opening and is exposed for surgical procedures; and (f) two releasable latch openings defined along opposite edges of the length of the cover housing and adapted to engage the releasable latching elements when a user moves the actuator in a forward direction to the forward latched position.

2. The device of claim 1 wherein the two releasable latch openings are located at about halfway along the length of the cover housing.

3. The device of claim 1 wherein the releasable latching means are adapted to prevent rearward travel of the sliding piece from the forward latched position if only one of the releasable latching elements are depressed so that it passes below an innermost edge of its releasable latch opening.

4. The device of claim 1 wherein the releasable latching means are adapted so that both releasable latching elements must be depressed so they pass below an innermost edge of a releasable latch opening to which the releasable latching element is engaged before spring means or actuator motion permits rearward travel of the sliding piece from the forward latched position.

5. The device of claim 1 wherein a permanent latch is adapted to permanently latch the sliding piece in one position along the length of the sliding bore.

6. The device of claim 5 wherein the permanent latch is adapted to latch the sliding piece into one position rearward of the rest position.

7. The device of claim 6 wherein the permanent latch comprises permanent latch extensions at each of the two legs and permanent latch receivers.

8. 1. A retractable scalpel device comprising:

(a) a cover housing with top and bottom edges and right and left sides along a length of the cover housing and defining a longitudinal sliding bore, the sliding bore having a blade opening defined in the cover housing at a forward end, and a slot extending through at least part of the left side of the cover housing;

(b) a sliding piece comprising a forward section, on which is fixed a scalpel blade and a slider legs section, where the slider legs section has a lateral extension through the slot and beyond the left side of the cover housing to form an actuator adapted to permit a user to move the sliding piece in forward and rearward motion in the slot and within the sliding bore;

(c) the slider legs section comprising a sliding section with lateral dimensions adapted to slidingly support the sliding piece in the sliding bore;

(d) the slider legs section further comprising two flexible legs extending rearward from the sliding section, where a rearward part of the legs are urged apart from one another and have a stepped extension urged against either a top or bottom surface of the sliding bore; and (e) two releasable latch openings defined along opposite edges of the length of the cover housing and adapted to engage the stepped extension when a user moves the actuator in a forward direction to the forward latched position.

9. The device of claim 8 wherein the two releasable latch openings are located at about halfway along the length of the cover housing.

10. The device of claim 8 wherein stepped extensions are adapted to prevent rearward travel of the sliding piece from the forward latched position if only one of the releasable latching elements are depressed so that it passes below an innermost edge of its releasable latch opening.

11. The device of claim 8 wherein the stepped extensions are adapted so that both stepped extensions must be depressed so they pass below an innermost edge of a releasable latch opening to which the stepped extension is engaged before actuator motion permits rearward travel of the sliding piece from the forward latched position.

12. The device of claim 8 wherein a permanent latch is adapted to permanently latch the sliding piece in one position along the length of the sliding bore.

13. The device of claim 12 wherein the permanent latch is adapted to latch the sliding piece into one position rearward of the rest position.

14. The device of claim 13 wherein the permanent latch comprises permanent latch extensions at each of the two legs and permanent latch receivers.

15. The device of claim 8 wherein spring means urge the sliding piece rearward so that in a rearward rest position the blade is covered by the cover housing and in a forward latched position the blade has passed though the blade opening and is exposed for surgical procedures.

* * * * *